United States Patent [19]

Utterberg

[11] Patent Number: 5,061,365

[45] Date of Patent: Oct. 29, 1991

[54] MEDICAL FLUID FLOW SET

[76] Inventor: David S. Utterberg, 1080 Chestnut St., San Francisco, Calif. 94109

[21] Appl. No.: 643,230

[22] Filed: Jan. 22, 1991

[51] Int. Cl.$^5$ .................... A61M 1/14; B01D 35/14; B01D 65/00
[52] U.S. Cl. .................................... 210/90; 210/137; 210/321.6; 604/5; 604/31; 604/67; 138/30
[58] Field of Search ............... 210/90, 97, 137, 195.2, 210/321.6; 604/5, 31, 52, 67, 4, 6; 138/30

[56] References Cited

U.S. PATENT DOCUMENTS

| | | | |
|---|---|---|---|
| 3,754,649 | 8/1973 | Palubniak et al. | 210/103 |
| 4,098,275 | 7/1978 | Consalvo | 604/44 |
| 4,486,189 | 12/1984 | Troutner et al. | 604/5 |
| 4,490,135 | 12/1984 | Troutner | 604/5 |
| 4,501,583 | 2/1985 | Troutner | 210/90 |
| 4,715,849 | 12/1987 | Gion et al. | 604/52 |

Primary Examiner—W. Gary Jones
Attorney, Agent, or Firm—Garrettson Ellis

[57] ABSTRACT

A medical fluid flow set comprises flexible flow tubing having a plastic "pillow" connected in-line with the flow tubing through opposed, generally parallel first and second longitudinal ports. By this invention, the plastic pillow comprises a single, blow-molded, integral piece with a third port communicating with the pillow at a point between the first and second ports. The third port tube extends laterally outwardly from the pillow and turns, typically by essentially a right angle to define an outer tube end having an axis essentially parallel to the first and second ports. A set branch line may be connected to the outer tube end. Such a pillow is manufactured by blow molding to provide an improved product over the prior art, at less cost.

7 Claims, 1 Drawing Sheet

MEDICAL FLUID FLOW SET

BACKGROUND OF THE INVENTION

The invention relates to an improved medical fluid flow set and method of manufacturing the same. Particularly, the invention may be used as arterial hemodialysis sets which carry a negative pressure pillow, as is customary in commercial embodiments of such sets.

Arterial sets are used in conjunction with hemodialyzers to convey blood from the patient to the hemodialyzer, where metabolic waste products such as urea, water, and creatinine are removed. Then, the blood flows from the hemodialyzer via a venous hemodialysis set back to the vein of the patient.

Conventionally, arterial sets for hemodialysis contain a negative pressure pillow, which pillow constitutes a small enlargement of the flow tubing of the arterial set, positioned in-line intermediate the ends of the set tubing. Typically, the pillow is of a wall thickness which is thick enough to at least partially collapse when predetermined negative pressure conditions are encountered in the arterial set. A branch line typically extends laterally outwardly from the conventional negative pressure pillow, to connect to a source of saline solution or the like for use in priming of the set, and also for rinsing back the blood from the set to the patient to minimize the loss of blood experienced by the patient during a hemodialysis procedure.

The collapse of the pillow at a certain negative pressure typically activates a microswitch with which the pillow is placed in contact, to stop or reduce blood pump speed until sufficient arterial set pressure is restored. It is to be understood that the term "negative pressure" is commonly used among those skilled in the art, and relates to a pressure which is less than atmospheric.

By the above means, it is assured that the hemodialysis system will not run dry of blood because of excessive roller pump speed, outpumping the capacity of the arterial set to draw blood from the patient.

Alternatively, a physiologic fluid source such as saline solution can be administered through the branch tube of the pillow instead of, or in addition to, slowing or stopping of the pump, in order to restore desired fluid pressure in the arterial set. This pillow is also typically placed in engagement with a microswitch, but it operates as part of an apparatus that permits saline solution or the like to be drawn into the blood circuit in the circumstance of negative pressure being encountered.

In the prior art, such pillows are made by typically injection molding of a tube having a side port for the branch tube. Then, molded or extruded bushings of smaller diameter are placed into the ends of the tube, so that the central portion of the pillow is of larger diameter, following which the bushings are bonded to the ends of the central tube. This is accomplished by heat sealing the ends of the central tube around the bushings using a well-known type of heat seal.

Such a structure, while having been used through the years, is relatively expensive, requiring the manufacture of precursor parts plus an assembly step involving heat sealing.

Blow molded pillows for medical fluid flow sets are also known in the prior art. In the specific blow molding process, a pillow having an enlarged, tubular central portion and smaller diameter end ports can be blow molded with a lateral, outwardly projecting dimple. After the blow molding step, the dimple is cut open in a further step, and a molded, tubular port is bonded into the cut area where the dimple originally was. Following this, the branch tube can be bonded to the molded port.

This blow molding process for pillows is also cumbersome, multistep, and rather expensive. Also, both of the above manufacturing techniques for pillows for use in flow sets result in pillows which are prone to leaking whenever inadequate seals are formed, and they also often exhibit thrombogenic characteristics because of the presence of sharp, internal corners.

In accordance with this invention, a pillow for a medical fluid flow set is provided in which the whole pillow can be made with a single blow molding step, rather than the multiple assembly steps of the prior art. Furthermore, the blow molded pillow comprises a single, integral piece with all of its respective port tubes, which significantly reduces the risk of leak formation during use of the set in which the pillow is emplaced.

Furthermore, the modifications used in this invention are of a nature that they provide little or no disturbance to other normal procedures of manufacture and use of medical fluid flow sets which include the pillow of this invention. Thus, medical fluid flow sets having the pillow of this invention may still be used with the present commercially available dialyzer units in present, commercially available dialysis machines. Essentially no modification of other equipment is required to accommodate the modified flow set of this invention. Also fewer sharp internal corners are found, for better blood handling.

DESCRIPTION OF THE INVENTION

In this invention, a medical fluid flow set is provided which comprises flexible flow tubing having a plastic "pillow" connected in-line with the flow tubing through opposed first and second longitudinal ports that are typically essentially parallel. In accordance with this invention, the plastic pillow of the set comprises a single, blow-molded, integral piece with a third port tube communicating with said pillow at a point between the first and second ports. In other words, the third port tube is an integrally molded part of the blow molded pillow. The third port tube extends laterally outwardly from the pillow, then turning to define an outer tube end which has an axis essentially parallel to the first and second ports.

A set branch line is connected with the outer tube end of the third port. When the medical fluid flow set which carries the pillow is an arterial hemodialysis set, the set branch line is typically a saline solution line for set priming and blood rinseback in a manner which is per se known.

Such a plastic pillow may be installed into the set in conventional manner, for example by means of automatic tube fitting machines which are known and which provide significant economies in the manufacture of medical fluid flow sets. This assembly is facilitated with the known, automatic tube fitting machines since all of the ports of the plastic pillow have axes which are essentially parallel, so that all tubes applied by the automatic tube fitting machines may be applied from essentially parallel directions.

Thus, the medical fluid flow set which carries the blow molded plastic pillow of this invention may be simply and easily assembled, while at the same time the blow molded plastic pillow of this invention may be manufactured at a substantially reduced cost compared with corresponding pillows of the prior art. Furthermore, the quality of the pillows of this invention is improved, since they tend to be far more leak resistant than the prior art pillows used in medical fluid flow sets.

The sets of this invention, carrying the inventive pillows, may be manufactured with the set containing a plastic pillow which is connected to a branch line and connected in-line with the flow tubing of the set. By this invention, one blow molds the pillow from a molten plastic parison while forming opposed, longitudinal ports in the parison by means of opposed, parallel first and second port-forming pins of the blow mold. One further simultaneously forms a third port tube in the parison that communicates with the pillow at a point between the opposed, longitudinal ports. The third port tube extends laterally outwardly from the point described above, and also turns to define an outer end section which extends generally parallel to the port-forming pins. The outer end section receives during the blow molding step a third port-forming pin, the third pin being positioned to extend essentially in the same direction as the first and second port-forming pins.

Thereafter, one connects the blow molded pillow thus formed at the opposed ports and the third port tube, respectively to the flow tubing and the branch line to assemble the set.

DESCRIPTION OF SPECIFIC EMBODIMENT

Figure 1:
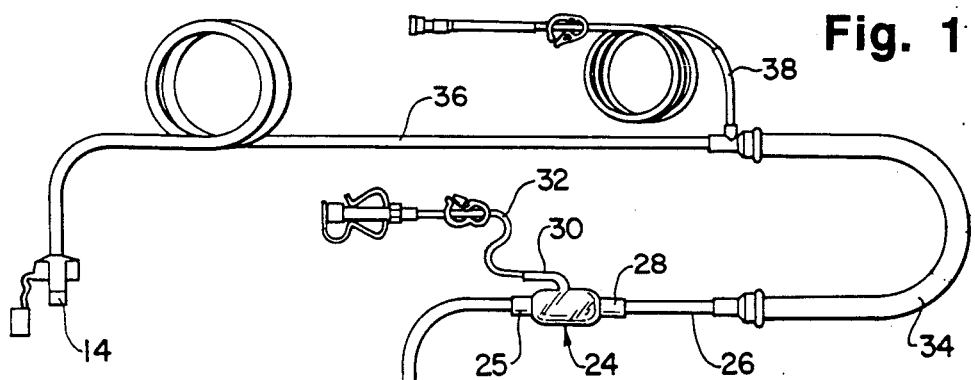
FIG. 1 is a plan view of an arterial blood tubing set for hemodialysis, which includes a plastic negative pressure pillow in accordance with this invention.

Referring to the drawings, an arterial blood flow set 10 is disclosed, for connection at end 12 with a fistula needle in the venous system of a patient by means of a luer connector or the like, and for connection at the other set end 14 with a dialyzer by means of a luer lock connector. The specific arterial set shown may be used in conjunction with a Gambro AK-10 dialyzer, for example, using techniques which are well-known to the art except as otherwise described herein.

Venous blood passes from the fistula needle through end 12 of arterial set 10, passing through flexible tubing 16, the flow of which may be controlled by a conventional on/off clamp 18. Injection site 20 is provided in a conventional manner for the administration of supplemental medications and the like as desired. Often, the tubing is stored in coils 22, as shown, to facilitate the initial storage thereof. The coils may be broken apart to lengthen the tube as needed.

Tube 16 terminates at a connection with first port 25 of negative pressure pillow 24, which is made in accordance with this invention. Tubing 26 is connected to negative pressure pillow 24 at port 28, which is opposed to the connection port 25. Angled branch port 30 is also provided to pillow 24, connecting with a conventional saline line 32.

Tubing 26 connects with conventional roller pump tubing 34, which, in turn, connects at its opposed end with set tubing 36, which carries end 14 and its connector. A second branch tubing 38 is provided in conventional manner for use as the heparin line.

Figure 2:
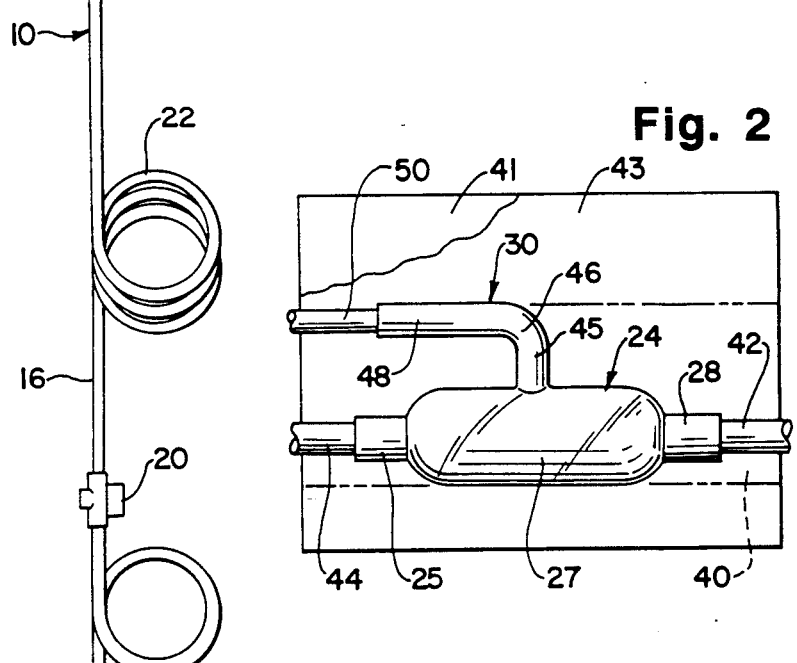
FIG. 2 is an elevational view showing the negative pressure pillow of FIG. 1 in the process of being blow molded.

Turning to the detailed view of negative pressure pillow 24 in FIG. 2, the pillow is shown in process of blow molding in a single step. Hot, tubular plastic parison 40 is placed between a pair of openable and closeable blow mold halves 41, 43 (the former blow mold half being shown substantially broken away) to press port of parison 40 together into the shape of pillow 24. At the same time, mandrel 42 is positioned so that portions of parison 40 collapse about the mandrel to form longitudinal port 28. Mandrel 42 may be hollow and may serve as the inflation port by which pillow 24 is held in inflated condition during the blowing process, as is conventional in blow molding. At the same time, mandrel 44 may be provided to form longitudinal port 25 in similar manner, so that a pair of opposed, longitudinal ports 25, 28 are formed in the pillow.

Additionally, the blow mold halves 41, 43 further define third, laterally extending port tube 30 which communicates with the enlarged chamber 27 of pillow 24 at a point between the first and second longitudinal ports 25, 28. Third port tube 30 comprises a laterally inward transversely extending section 45, at the end of which a right angle bend 46 is defined, followed by a longitudinally extending end section 48.

Third mandrel 50 is provided to penetrate the end of end section 48, to assist in the definition of its end in a manner similar to the way that mandrels 42, 44 assist in the definition of the ends of longitudinal port tubes 25, 28.

Accordingly, in a single "shot" the pillow 24 of this invention may be manufactured by blow molding in a process that is otherwise conventional except as indicated herein, to form a plastic pillow that may be used as a negative pressure pillow in medical fluid flow sets. The angled configuration of the side port 30 provides significant advantages both of manufacture and use: specifically in that the pillow may be made in a single shot with a blow mold in which tube-forming mandrels are present which are all aligned parallel to each other. This provides a great manufacturing advantage for the efficient manufacture of a one-piece structure, which previously for years has had to be made by multi-step processes and which has resulted in products that are subject to leakage and other disadvantages.

While an improved plastic pillow is manufactured in accordance with this invention, it also is manufactured at a reduction of cost over the prior art structures.

Figure 3:
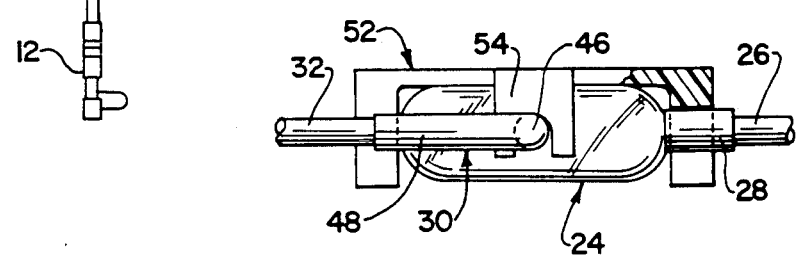
FIG. 3 is a fragmentary, elevational view showing the negative pressure pillow of FIG. 1 positioned in a conventional microswitch housing of a hemodialysis system.

As shown in FIG. 3, the negative pressure pillow 24 of this invention and of set 10 is shown in its operative position in a dialysis machine, specifically a Gambro AK-10 dialysis machine. Pillow 24 is shown to be mounted in a conventional microswitch housing 52 of the dialysis machine, third port tube 30 being shown to be retained at approximately its right angle turn 46 by means of bracket 54, which bracket is part of the dialysis machine. It can be seen that the blow molded pillow of this invention, while of a different shape from the prior art negative pressure pillows, can be adapted to fit easily into conventional dialysis machines without modification.

The dialysis, sets which make use of the negative pressure pillows 24 of this invention may be used to replace prior art sets without any significant difficulty or modification of the equipment with which they are used.

Port tubes 25, 28, 30 of pillow 24 may be connected to the respective tubings 16, 26, and 32 in entirely conventional manner, typically solvent sealing.

Pillow 24 of this invention may be typically made of a plastic such as polyvinyl chloride, and may be of a wall thickness comparable to conventional negative pressure pillows, so that the negative pressure pillow of this invention will collapse upon exposure to an internal negative pressure of a predetermined amount. Thus, the pillow 24 can be used in the conventional microswitch housing 52. The collapse of the pillow does not have to be a complete collapse, but just sufficient to operate the microswitch of housing 52, in a manner similar to the pillows of the prior art.

The above has been offered for illustrative purposes only, and is not intended to limit the scope of the invention of this application, which is as defined in the claims below.

That which is claimed is:

1. In a medical fluid flow set which comprises flexible flow tubing having a plastic "pillow" connected in-line with said flow tubing through opposed first and second longitudinal ports, the improvement comprising, in combination:

said plastic pillow comprising a single, blow-molded, integral piece with a third port tube communicating with said pillow at a point between said first and second ports, said third port tube extending laterally outwardly from said pillow and turning to define an outer tube end having an axis essentially parallel to said first and second ports, and a branch line connected with said outer tube end.

2. The medical fluid flow set of claim 1 which is an arterial hemodialysis set.

3. The medical fluid flow set of claim 2 in which said set branch line is a saline solution line for set priming and blood rinseback.

4. The medical fluid flow set of claim 1 in which said plastic pillow has a wall thickness sufficient to permit at least partial collapse upon exposure to an internal negative pressure of a predetermined amount.

5. A plastic "pillow" for connection in-line with flow tubing, said plastic pillow comprising opposed first and second longitudinal ports and a central section of enlarged transverse dimension relative to said ports, said plastic pillow and ports comprising a single, blow-molded, integral piece with a third port tube communicating with said pillow at a point between said first and second ports, said third port tube extending laterally outwardly from said pillow and turning to define an outer tube end having an axis essentially parallel to said first and second ports.

6. The plastic pillow of claim 5 in which the wall thereof has a thickness sufficient to permit its collapse upon exposure to an internal negative pressure of a predetermined amount.

7. The plastic pillow of claim 5 which is made of polyvinyl chloride.

* * * * *